United States Patent [19]
Nakatsu et al.

[11] Patent Number: 5,788,828
[45] Date of Patent: Aug. 4, 1998

[54] APPARATUS FOR DETECTING ANIONS IN WATER

[75] Inventors: Masato Nakatsu; Syu Nakanishi; Akira Fukunaga; Takayuki Saito; Kanroku Chounan, all of Kanagawa, Japan

[73] Assignee: Ebara Corporation, Tokyo, Japan

[21] Appl. No.: 757,667

[22] Filed: Nov. 29, 1996

[30] Foreign Application Priority Data

Nov. 30, 1995 [JP] Japan .................................. 7-334226
Jun. 7, 1996 [JP] Japan .................................. 8-166685

[51] Int. Cl.$^6$ ............................................. B01D 35/06
[52] U.S. Cl. ........................... 204/632; 204/647; 422/82.02
[58] Field of Search .................................. 204/632, 647, 204/524; 422/82.02

[56] References Cited

U.S. PATENT DOCUMENTS 4,814,281  3/1989  Byers ............................ 422/82.02
5,593,554  1/1997  Yamanaka et al. ............. 204/632

FOREIGN PATENT DOCUMENTS

5-264393  10/1993  Japan .
5-264492  10/1993  Japan .
6-82173   3/1994   Japan .

Primary Examiner—Bruce F. Bell
Attorney, Agent, or Firm—Wenderoth, Lind & Ponack, L.L.P.

[57] ABSTRACT

An improved apparatus for detecting anions in water includes an electrical continuous ion-exchange unit comprising an anode compartment and a cathode compartment which are spaced apart by an alkali removing compartment packed with a cation exchanger defined by two cation-exchange membranes. Each of the said anode compartment, cathode compartment and alkali removing compartment is provided with a passageway through which water is admitted and a passageway through which the treated water is discharged. The passageway through which the treated water is discharged from the alkali removing compartment is equipped with an instrument for measuring the specific resistance or electrical conductivity of the treated water. The alkali removing compartment may be replaced by one or more cation-exchange membranes or a treatment compartment defined by two or more cation-exchange membranes, and the passageway through which the treated water is discharged from the anode compartment is equipped with an instrument for measuring the specific resistance or electrical conductivity of the treated water. The apparatus does not require replacement of ion-exchange resins, achieves correct measurements with a simple operation and yet functions as an inexpensive salt detector.

11 Claims, 5 Drawing Sheets

APPARATUS FOR DETECTING ANIONS IN WATER

BACKGROUND OF THE INVENTION

This invention relates to an apparatus for detecting anions in water, more particularly, to a detector of anions represented by chloride ions which is capable of sensing the leakage of cooling water (seawater) from condensers in thermal and nuclear power plants.

Figure 4:
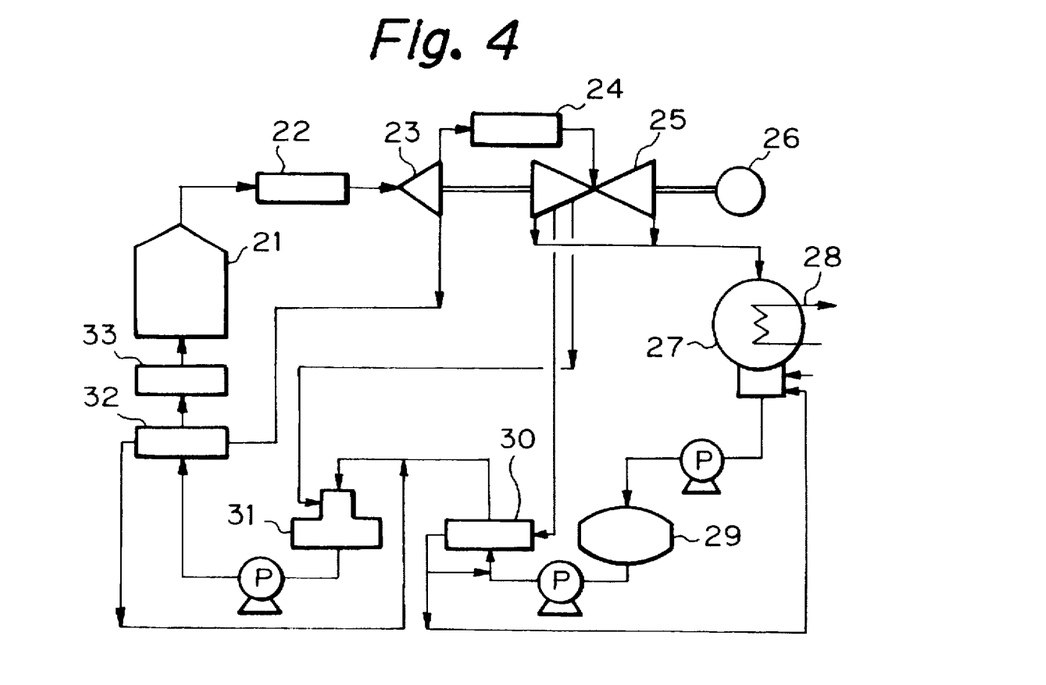
FIG. 4 is a flowsheet for the circulation of water feed to a boiler in a thermal power plant.

A flowsheet for the circulation of water supplied to a boiler in a thermal or nuclear power plant is shown in FIG. 4. The boiler 21 generates high-temperature and high-pressure steam, which is directed into steam turbines 23 and 25. The exhaust steam from the turbine 25 is fed into a condenser 27 where it is condensed into water, which is returned to the boiler 21. In order to remove corrosion products and other impurities which build up in the circulating water, a purifier (desalter of condensed water) 29 is provided in the system. The condenser 27 in the circulation system is evacuated on the steam side whereas seawater 28 is used as cooling water; therefore, if pinholes occur in small pipes in the condenser, the seawater will enter the steam side to cause a marked increase in the salt concentration. As a result, the load on the condensed water desalter 29 increases, exceeding its allowable limit if more of the seawater leaks. It is therefore necessary to detect any leakage of the seawater by means of a salt detector. Three major methods to detect the leaking seawater are the measurement of specific resistance or electrical conductivity, the use of a sodium monitor, and atomic absorption spectroscopy.

The first approach which involves the measurement of a specific resistance or electrical conductivity requires a cation-exchange resin for the following reason: in order to control the corrosion in the system, ammonia and hydrazine are usually added to the circulating water in such amounts as to provide an ammonia concentration of about 1 ppm as $NH_4$ and a hydrazine concentration of about 100 ppb as $N_2H_4$. As a result, the specific resistance of the circulating water is low but its electrical conductivity is high and, hence, even if the seawater leaks in a slight amount to cause a small increase in the salt concentration, the as-measured value of the change is so small that it is difficult to know the correct amount of the seawater leakage. To deal with this problem, the common practice adopted today is to pass the water through a regenerable cation-exchange resin such that not only the initially present cationic ammonia and hydrazine but also the entering cationic component such as sodium ions in the NaCl which is the main component of the leaking seawater and the specific resistance or the electrical conductivity of acid which are primarily due to HCl is measured.

The second approach which involves a sodium monitor is based on an ion-selective glass electrode.

The third approach which relies upon atomic absorption spectroscopy is not capable of constant monitoring since the water of interest has to be sampled and brought back to a laboratory for analysis.

The three approaches described above have their own problems. The first approach which involves the measurement of the electrical conductivity of an acid requires a cation-exchange resin but the resin is no longer functional if it adsorbs more than a specified amount of ions. The ineffective resin must be either regenerated or replaced by a new one but the costs of these operations and resins are substantial.

The sodium monitor employed in the second approach uses a glass electrode, so it suffers from the disadvantage that in the low-concentration range, the electromotive force of the electrode decreases to such an extent that the sensitivity of the monitor deviates from Nernst's equation toward a smaller value and, in addition, the use of a potassium chloride solution as an electrolyte for the reference electrode can potentially produce an error in the positive direction on account of potassium ions that diffuse toward the sample water. What is more, iron oxide or hydroxide which are commonly referred to as "cladding" may contaminate the electrode surface to lower the sensitivity of the monitor.

The third approach which depends on atomic absorption spectroscopy cannot be implemented with a portable device which can be installed at the site of analysis, so the water of interest has to be sampled and brought back to the laboratory for analysis. An alternative method is one that employs an ion chromatographic analyzer. Although the size of this device is comparatively smaller, it requires cumbersome procedures to prepare reagents for analysis and the device is as expensive as the atomic absorption spectroscopic apparatus.

SUMMARY OF THE INVENTION

The present invention has been accomplished under these circumstances and has as an object providing an apparatus for detecting anions in water which does not require replacement of ion-exchange resins, that is free from the problem of contamination by solid suspended matter such as "cladding", that achieves correct measurements by a simple operation and which yet functions as an inexpensive salt detector.

The stated object of the invention can be attained by an apparatus for detecting anions in water which comprises an electrical continuous ion-exchange unit comprising an anode compartment and a cathode compartment which are spaced apart by an alkali removing compartment packed with a cation exchanger defined by two cation-exchange membranes, each of the anode and cathode compartments, as well as the alkali removing compartment being provided with a passageway through which water is admitted and a passageway through which the treated water is discharged. The passageway through which the treated water is discharged from the alkali removing compartment is equipped with an instrument for measuring the specific resistance or electrical conductivity of the treated water.

In a preferred embodiment, the passageway through which water is admitted into the anode compartment is connected to a pipe for feeding pure water or a bypass pipe connecting to the passageway through which the treated water is discharged from the alkali removing compartment.

If the anode compartment is to be supplied with water other than pure water or the treated water, one of the two cation-exchange membranes which is on the anode side must be a hydrogen ion-permselective or a bipolar membrane.

The stated object of the invention can also be attained by an apparatus for detecting anions in water which comprises an electrical continuous ion-exchange unit comprising an anode compartment and a cathode compartment which are spaced apart by one or more cation-exchange membranes. Each of the anode and cathode compartments is provided with a passageway through which water is admitted and a passageway through which the treated water is discharged. The passageway through which the treated water is discharged from the anode compartment is equipped with an instrument for measuring the specific resistance or electrical conductivity of the treated water.

The stated object of the invention can also be attained by an apparatus for detecting anions in water which comprises an electrical continuous ion-exchange unit comprising an anode compartment and a cathode compartment which are spaced apart by a treatment compartment defined by two or more cation-exchange membranes. Each of said anode and cathode compartments, as well as the treatment compartment is provided with a passageway through which water is admitted and a passageway through which the treated water is discharged. The passageway through which the treated water is discharged from the treatment compartment is equipped with an instrument for measuring the specific resistance or electrical conductivity of the treated water.

DETAILED DESCRIPTION OF THE INVENTION

The present invention will now be described in detail with reference to the accompanying drawings.

Figure 1:
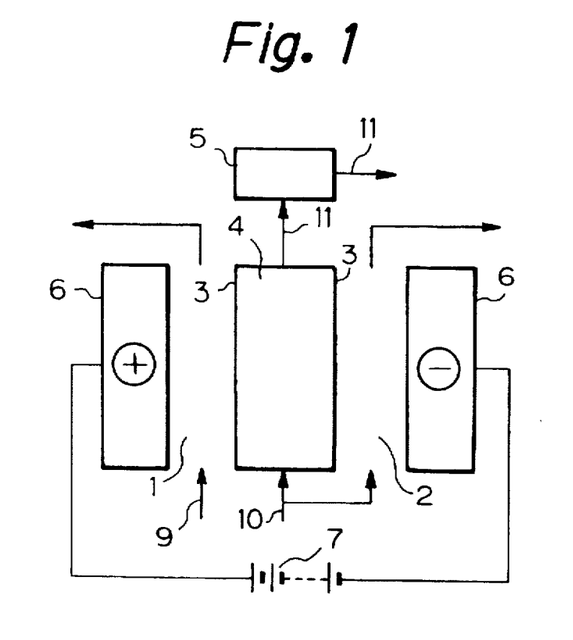
FIG. 1 is a schematic diagram showing an example of the detecting apparatus of the invention.

FIG. 1 is a schematic diagram showing an example of the detecting apparatus of the invention. The system shown in FIG. 1 uses two ordinary cation-exchange membranes and pure water. A feed of sample water 10 is admitted into an adjacent or alkali removing compartment 4 defined by two cation-exchange membranes 3 and into a cathode compartment 2, whereas pure water 9 is admitted into an anode compartment 1. The alkali removing compartment 4 has a cation exchanger inserted thereinto and the treated water 11 from which alkalies have been removed is monitored with a specific resistance meter 5 such that the chloride ions in the treated water are detected in terms of the change in the measured value of specific resistance. The alkali ions such as $NH_4^+$ and $Na^+$ that have been adsorbed on the cation exchanger are pumped by an electrode 6 connected to a dc power supply 7 such that they are continuously passed through the cation-exchange membrane 3 on the cathode side to migrate into the water in the cathode compartment. Therefore, the ion-exchange capacity of the cation exchanger will not deteriorate as in the case of ion-exchange resins and the system can be operated for almost an indefinite period of time.

Figure 2:
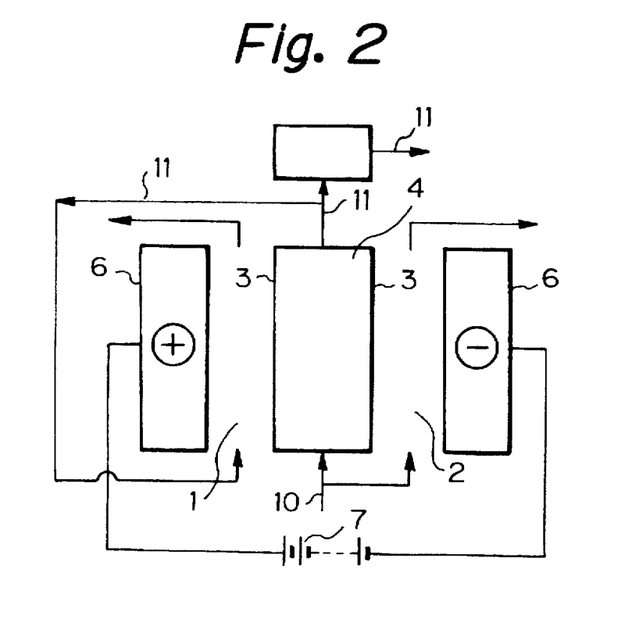
FIG. 2 is a schematic diagram showing another example of the detecting apparatus of the invention.

FIG. 2 shows another example of the detecting apparatus of the invention. The anode compartment 1 in the system shown in FIG. 2 is not supplied with pure water 9 but treated water 11. This is because in substantial absence of cations other than hydrogen ions in the treated water 11, no cations except hydrogen ions will migrate toward the adjacent or alkali removing compartment 4.

Figure 3:
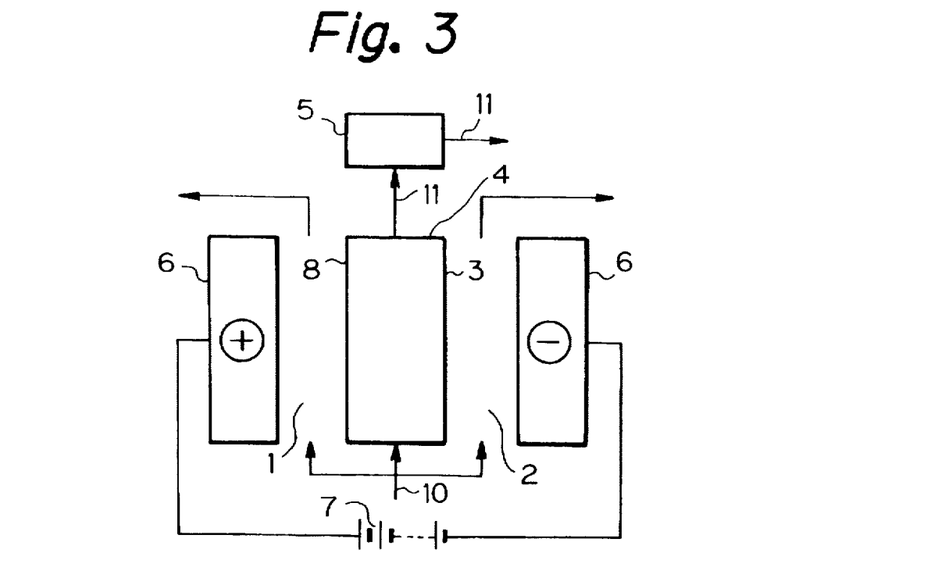
FIG. 3 is a schematic diagram showing yet another example of the detecting apparatus of the invention.

FIG. 3 shows yet another example of the detecting apparatus of the invention. The system shown in FIG. 3 uses a hydrogen ion-permselective or a bipolar membrane 8 is used as the cation-exchange membrane on the anode side. This design eliminates the need for feeding pure water into the anode compartment and the sample water 10 can instead be admitted.

In FIGS. 1 and 2, the anode compartment is supplied with pure water and the alkali-free water, respectively, for the following reason. If the anode compartment is supplied with sample water containing cations, the treated water will not be thoroughly freed of alkalies and this is probably because cations are entrapped to remain in the cation exchanger as they migrate from the anode compartment to pass through the cation-exchange membrane on the anode side. If a hydrogen ion-permselective or a bipolar membrane is used as the cation-exchange membrane on the anode side as in the case shown in FIG. 3, no cations will migrate from the anode compartment into the alkali removing compartment. This is why the sample water rather than pure water can be admitted into the anode compartment in the FIG. 3 design.

We next describe the basic principle for the operation of the systems shown in FIGS. 1–3. The detecting apparatus of the invention is basically the combination of an electrodialyzer with a specific resistance meter. A problem with an ordinary electrodialyzer is that if the water circulating in the system shown in FIG. 4 has low concentrations of about 1 ppm as $NH_4^+$ and abut 100 ppb as $N_2H_4$, an electric current will flow with so much difficulty that a higher voltage will result, which is uneconomical as exemplified by the need to employ a bulky dc power supply unit. To deal with this problem, a cation exchanger is inserted between two cation-exchange membranes, thereby achieving a marked decrease in the voltage requirement. This is probably due to the transfer of ions by means of ion-exchange groups ($—SO_3H$) in the cation exchanger.

If, as in the system shown in FIG. 1, both cation-exchange membranes of the ordinary type are used with pure water being allowed to flow into the anode compartment 1, the ammonia and hydrazine components in the sample water 10 are entrapped with the cation exchanger and pass through the cation-exchange membrane 3 on the cathode side to migrate toward the cathode compartment 2. Since the water in the anode compartment 1 is pure water 9, it has no ion components; in addition, no cations other than hydrogen ions will migrate from the anode compartment 1 to the alkali removing compartment 4 and, hence, the treated water 11 is pure water.

In the system shown in FIG. 2, the anode compartment 1 is supplied with the treated water 11 and since this water contains no cations other than hydrogen ion, the treated water 11 is again pure water as in the case just described above. If a small amount of sodium chloride enters the sample water 10, the increase of sodium chloride level is only a few ppb as NaCl in a unit concentration of 1 ppm as $NH_4^+$ and, accordingly, the electrical conductivity of the sample water 10 per se will hardly change.

On the other hand, the treated water 11 is free from cations ($NH_4^+$, $N_2H_4$ and $Na^+$) but not of $Cl^-$ which is an anion. As a result, the electrical conductivity of the treated water changes by an amount that corresponds to the entrance of Cl⁻. This change in electrical conductivity is greater than the change in NaCl of the same equivalent amount (i.e., the electrical conductivity of acid is greater) because H⁺ has a greater electrical conductivity than Na⁺ for a given equivalent amount to thereby contribute a more definite change in electrical conductivity. Electrical conductivity is the reciprocal of specific resistance and whichever parameter may be measured to assure satisfactory performance of the detecting apparatus of the invention.

The cation-exchange membrane on the anode side may be a hydrogen ion-permselective or a bipolar membrane 8 as shown in FIG. 3. In this case, there is no need to use pure water and sample water 10 can be admitted into all passageways. The reaction taking place in the water in the cathode compartment is the same as in the system shown in FIG. 1 and the water in the anode compartment contains $NH_4^+$ but this ion will not pass through the hydrogen ion-permselective or bipolar membrane 8 which transmits (generates) only hydrogen ions. As a result, pure water is produced as the treated water 11.

In the cases shown in FIGS. 1–3, the water to be supplied into each of the anode compartment, cathode compartment and alkali removing compartment flows at a rate of 0.5–5 m/s and the system will exhibit normal performance if the flowrate is within the stated range.

The present invention also provides a detecting apparatus in which anode and cathode compartments are separated by one or more ion-exchange membranes and two examples of this system will now be described with reference to FIGS. 5 and 6.

Figure 5:
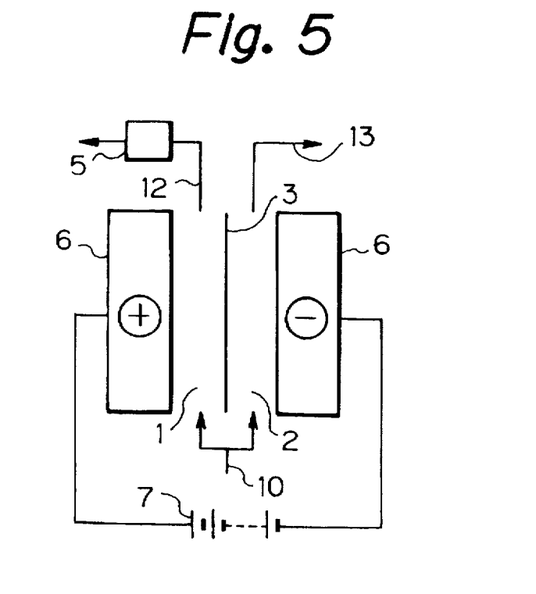
FIG. 5 is a schematic representation of still another example of the detecting apparatus of the invention.

In the system shown in FIG. 5, sample water 10 is admitted into an anode compartment 1 which is the adjacent compartment and which is separated from a cathode compartment 2 by means of a single cation-exchange membrane 3 and water 12 leaving the anode compartment after alkali removal is monitored with a specific resistance meter 5 such that the chloride ions in the sample water are detected in terms of the change in the measured value of specific resistance of the treated water 12. In the system shown in FIG. 5, the alkali ions such as $NH_4^+$ and $Na^+$ are pumped by an electrode 6 connected to a dc power supply 7 such that they are continuously passed through the cation-exchange membrane 3 on the cathode side to migrate toward the cathode compartment 2. Therefore, the ion-exchange capacity of the cation-exchange membrane 3 will not deteriorate as in the case of ion-exchange resins and the system can be operated for an almost indefinite period of time.

The electrolysis of water may occasionally cause the generation of oxygen or release of metal ions from the anode plate. If oxygen (bubbles) enters a specific resistance meter, its reading will fluctuate to make correct monitoring impossible. On the other hand, released metal ions will lower the reading of specific resistance, eventually producing errors in the positive direction. To prevent the first problem, the pressure in the anode compartment is increased above 0.1 kg/cm² or two cation-exchange membranes 3 may be employed as shown in FIG. 6 such that the specific resistance of the treated water 11 from a treatment compartment 14 (forming the adjacent compartment) defined by these membranes is measured with the specific resistance meter 5. The latter structure is also effective in solving the second problem due to the release of metal ions.

Figure 6:
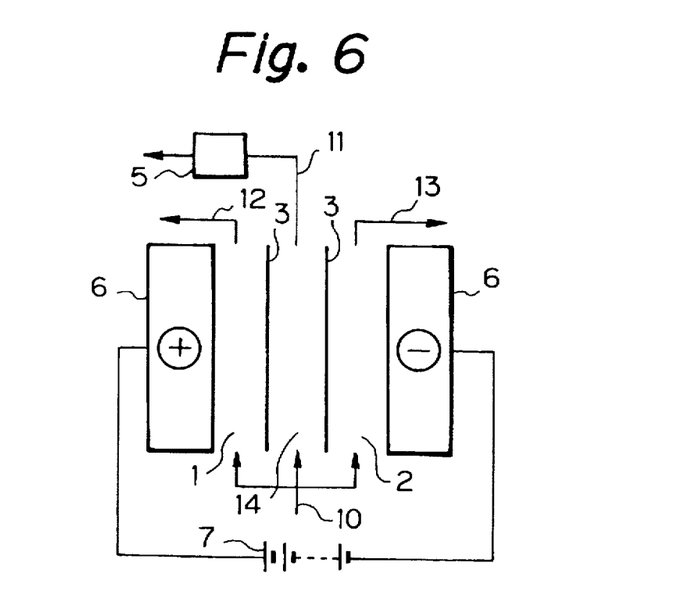
FIG. 6 is a schematic representation of a further example of the detecting apparatus of the invention.

In the system shown in FIG. 6, the alkali ions in the anode compartment 1 pass through the cation-exchange membrane 3 on the anode side to migrate toward the treatment compartment 14, whereas the alkali ions in the treatment compartment 14 will pass through the cation-exchange membrane 3 on the cathode side to migrate toward the cathode compartment 2. Thus, all alkali ions present will migrate to the cathode compartment 2, whereby both the water 12 in the anode compartment and the treated water 11 become alkali-free. The generation of air bubbles and the release of metal ions are phenomena that only take place on the electrode surfaces and the treatment compartment 14 defined by the two cation-exchange membranes 3 will in no way be affected by these phenomena. In addition, the systems shown in FIGS. 5 and 6 have no ion exchanger packing and, hence, are immune to contamination by solid suspended matter such as "cladding".

We will next describe the basic principle for the operation of the systems shown in FIGS. 5 and 6. Like the systems shown in FIGS. 1–3, the detecting apparatus shown in each of FIGS. 5 and 6 is basically the combination of an electrodialyzer with a specific resistance meter. The system shown in FIG. 5 uses the single cation-exchange membrane 3 and the distance between anode and cathode plates is reduced to less than 3 mm, thereby lowering the voltage requirement. The inter-electrode distance of the system shown in FIG. 6 is also reduced to 3 mm, which is small enough to lower the voltage requirement without packing the treatment compartment with an ion exchanger.

If the anode compartment 1 is separated from the cathode compartment 2 by the single cation-exchange membrane 3 as shown in FIG. 5, the ammonia and hydrazine components in the sample water 10 pass through the cation-exchange membrane 3 to migrate toward the cathode compartment 2. If a small amount of sodium chloride enters the sample water 10, the increase of sodium chloride level is only a few ppb as NaCl in a unit concentration of 1 ppm as $NH_4^+$ and, hence, the specific resistance of the sample water per se will hardly change. On the other hand, the water 12 in the anode compartment is free from cations ($NH_4^+$, $N_2H_4$ and $Na^+$) but not of Cl⁻ which is an anion. As a result, the specific resistance of the water 12 changes by an amount corresponding to the entrance of Cl⁻. This change in specific resistance is greater than the change in NaCl of the same equivalent amount (i.e., the specific resistance of acid is greater) because H⁺ has a greater electrical conductivity than Na⁺ for a given equivalent amount to thereby contribute a more definite change in specific resistance.

If two cation-exchange membranes 3 are used as shown in FIG. 6, the air bubbles that are evolved from the anode plate as a result of the electrolysis of water and the metal ions that are released from the same anode plate for the same reason are prevented by the cation-exchange membrane 3 from entering the treated water, which contributes to more precise measurement of specific resistance. In the system shown in FIG. 6, the ammonia and hydrazine components in the sample water 10 pass through the cation-exchange membrane 3 on the anode side to migrate toward the treated compartment 14. Subsequently, the ammonia and hydrazine components in the treatment compartment will pass through the cation-exchange membrane 3 on the cathode side to migrate toward the cathode compartment 2. These migrations take place continuously until both the water 12 in the anode compartment and the treated water 11 become alkali-free. If sodium chloride enters the sample water, Na⁺ will migrate to the cathode compartment 2 whereas Cl⁻ remains in the anode compartment 1 and the treatment compartment 14 such that only Cl⁻ is contained in the treated water 11 to materialize the change in specific resistance.

Figure 7:
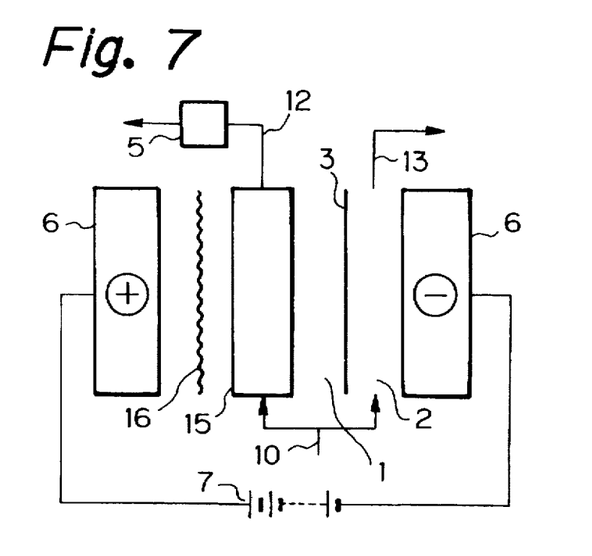
FIG. 7 is a schematic representation of yet another example of the detecting apparatus of the invention.

It is also within the scope of the invention to modify the detecting apparatus shown in FIG. 5 in such a way that a cation exchanger is inserted into the anode compartment as shown in FIG. 7. In the system shown in FIG. 7, the anode compartment 1 and the cathode compartment 2 are partitioned by the single cation-exchange membrane 3 and a cation exchanger 15 is inserted into the anode compartment 1 such that the water 12 emerging from the anode compartment via the cation exchanger 15 is monitored with a specific resistance meter to detect the chloride ions in the sample water. The design illustrated in FIG. 7 is capable of reducing the voltage between electrode plates, thereby contributing to a further reduction in power consumption. Shown by 16 in FIG. 7 is an insulating net which prevents either electrode plate from contacting the ion exchanger. If either electrode plate contacts the ion exchanger, heat is generated and the ion exchanger will scorch, failing to perform satisfactorily.

In the cases shown in FIGS. 5–7, the water to be supplied into each of the anode compartment, cathode compartment and alkali removing compartment flows at rate of 0.5–5 m/s and the system will exhibit normal performance if the flowrate is within the stated range.

The following examples are provided for the purpose of further illustrating the present invention but are in no way to be taken as limiting.

EXAMPLE 1

An experiment was conducted with the apparatus and operational flow that are shown in FIG. 1.

Pure water produced by treatment with a mixed-bed ion-exchange resin was adjusted to have a concentration of 1.1 ppm as $NH_4^+$ and the thus conditioned solution was mixed with NaCl to prepare a feed of sample water. The NaCl concentration of the sample water was varied and the specific resistance of the treated water was measured at various NaCl levels. The water supplied to the anode compartment was pure water that was produced by a similar treatment with a mixed-bed ion-exchange resin to a specific resistance of 18.25 MΩ·cm.

Figure 8:
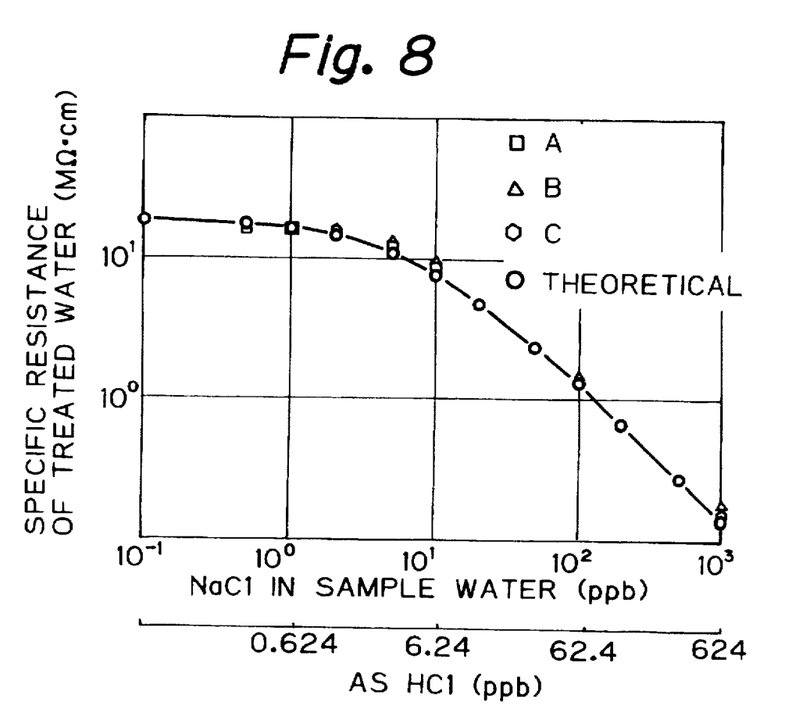
FIG. 8 is a graph showing the results of Examples 1–3 by the relationship between the concentration of NaCl in the sample water and the specific resistance of the treated water.

FIG. 8 shows the specific resistance of the treated water as a function of the NaCl concentration in the sample water. As a result of the treatment conducted in Example 1 and subsequent Examples, the NaCl in the sample water would turn to HCl, so the HCl concentration calculated from the NaCl level is also plotted on the horizontal axis of the graph in FIG. 8. The data obtained in Example 1 are represented by open squares A and have good agreement with the theoretical line. The inter-electrode voltage was 96 V at a current density of 35 $mA/dm^2$.

EXAMPLE 2

An experiment was conducted with the apparatus and operational flow that are shown in FIG. 2.

The operating procedure was essentially the same as in Example 1, except that the treated water was fed into the anode compartment. The data obtained in Example 2 are represented by open triangles B in FIG. 8 and they are in substantial agreement with the theoretical line, except that the specific resistance of the treated water had a tendency to deviate slightly toward higher values. The inter-electrode voltage was 95 V at a current density of 35 $mA/dm^2$.

EXAMPLE 3

An experiment was conducted with the apparatus and operational flow that are shown in FIG. 3.

The operating procedure was essentially the same as in Example 1, except that the anode compartment was supplied with water of the same quality as the sample water. The data obtained in Example 3 are represented by open hexagons C in FIG. 8 and they are in good agreement with the theoretical line. The inter-electrode voltage was 22 V at a current density of 35 $mA/dm^2$.

The inter-electrode voltage was substantially the same in Examples 1 and 2 but by far smaller in Example 3.

EXAMPLE 4

An experiment was conducted with the apparatus and operational flow that are shown in FIG. 5.

Pure water produced by treatment with a mixed-bed ion-exchange resin was adjusted to have a concentration of 1.1 ppm as $NH_4^+$ and the thus conditioned solution was mixed with Nacl to prepare a feed of sample water. The NaCl concentration of the sample water was varied and the specific resistance of the treated water was measured at various NaCl levels.

Figure 9:
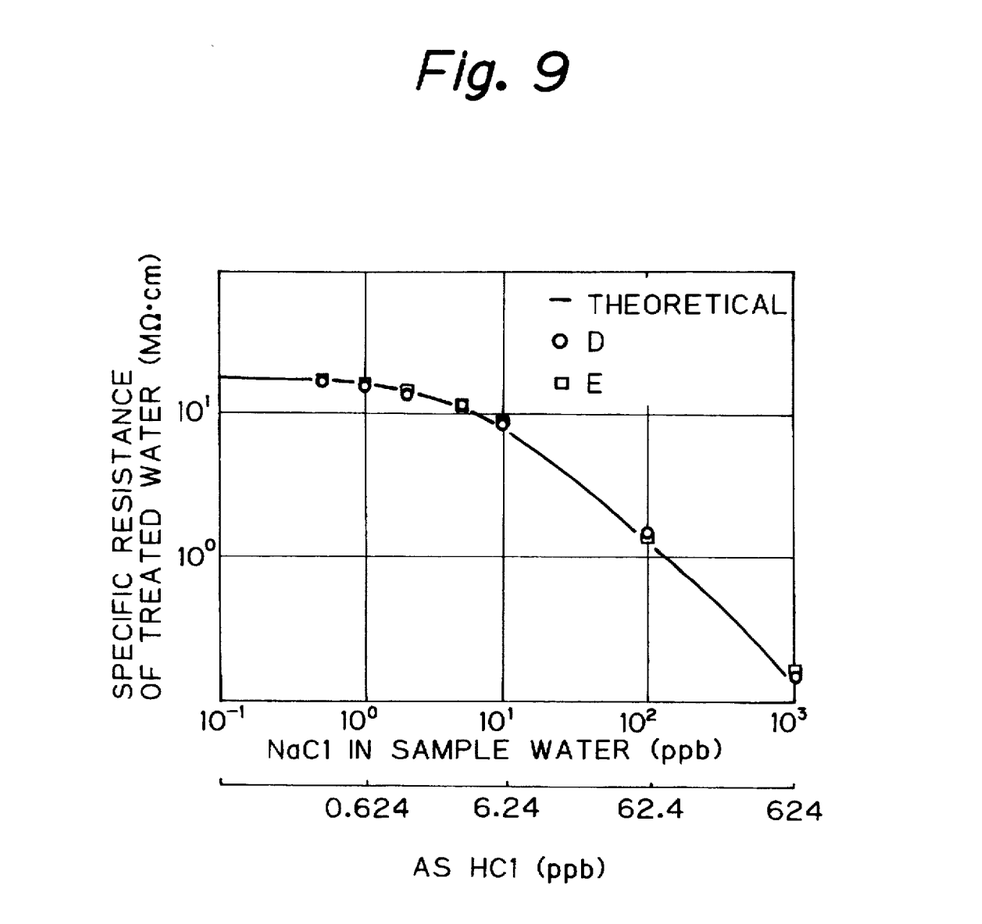
FIG. 9 is a graph showing the results of Examples 4 and 5 by the relationship between the concentration of NaCl in the sample water and the specific resistance of the treated water.

FIG. 9 shows the specific resistance of the treated water as a function of the NaCl concentration in the sample water. As a result of the treatment conducted in Example 4 and subsequent Examples, the NaCl in the sample solution would turn to HCl, so the HCl concentration calculated from the NaCl level is also plotted on the horizontal axis of the graph in FIG. 9. The data obtained in Example 4 are represented by open circles D and have good agreement with the theoretical line. The inter-electrode voltage was 82 V at a current density of 42 $mA/dm^2$.

EXAMPLE 5

An experiment was conducted with the apparatus and operational flow that are shown in FIG. 6.

The operating procedure was essentially the same as in Example 4, except that the treated water the specific resistance of which was measured did not emerge from the anode compartment but from the treatment compartment. The data obtained in Example 6 are represented by open squares E in FIG. 9 and they are in good agreement with the theoretical line. The inter-electrode voltage was 100 V at a current density of 42 $mA/dm^2$.

In each of Examples 1–5, the experiment was conducted at atmospheric pressure and at room temperature, with the flowrate being controlled at 2.0 m/s. The current density was so adjusted as to produce a voltage not higher than 100 V.

The detecting apparatus of the invention is capable of measuring trace levels of chlorine concentration in alkali solutions that contain no anions other than hydroxide ions. Compared to the prior art version using cation-exchange resins, the apparatus is capable of continuous measurements without the need to replace resins that have deteriorated in ion-exchange capacity. In addition, the apparatus is capable of more sensitive detection than a sodium monitor and serves as a salt detector that is considerably less costly than other analyzers.

If the apparatus is modified not to use ion exchangers but use only ion-exchange membranes, it becomes highly immune to the contamination by "cladding" and, hence, is free from the problem of clogging.

Because of these advantages, the detecting apparatus of the invention is particularly suitable for use in sensing the leakage of cooling water (seawater) from condensers in thermal or nuclear power plants.

What is claimed is:

1. An apparatus for detecting anions in water containing a small amount of ammonia and hydrazine, said apparatus comprising:

an electrical continuous ion-exchange unit comprising:
 a cathode compartment having a first inlet passageway and a first outlet passageway in fluid communication with said first inlet passageway; and
 an adjacent compartment having a second inlet passageway and a second outlet passageway in fluid communication with said second inlet passageway, said adjacent compartment being adjacent to said cathode compartment and being separated therefrom by a first cation exchange membrane;
an instrument, disposed in said second outlet passageway, for measuring a specific resistance or electrical conductivity of water; and
said apparatus being free of an electrolyte supply unit.

2. An apparatus as claimed in claim 1, wherein said adjacent compartment comprises an anode compartment.

3. An apparatus as claimed in claim 2, wherein said adjacent compartment is free of an ion exchanger.

4. An apparatus as claimed in claim 1, wherein said adjacent compartment is free of an ion exchanger.

5. An apparatus as claimed in claim 1, wherein said electrical continuous ion-exchange unit further comprises an anode compartment adjacent to said adjacent compartment and on a side thereof opposite said cathode compartment, said anode compartment having a third inlet passageway and a third outlet passageway in fluid communication with said third inlet passageway.

6. An apparatus as claimed in claim 5, wherein said anode compartment is separated from said adjacent compartment by a second cation exchange membrane.

7. An apparatus as claimed in claim 5, wherein said anode compartment is separated from said adjacent compartment by a hydrogen ion-permselective membrane or a bipolar membrane.

8. An apparatus as claimed in claim 1, wherein said adjacent compartment has packed therein an ion exchanger.

9. An apparatus as claimed in claim 1, further comprising a pure water feed pipe in fluid communication with said second inlet passageway of said adjacent compartment.

10. An apparatus as claimed in claim 1, further comprising a bypass pipe in fluid communication with said second outlet passageway of said adjacent compartment.

11. An apparatus as claimed in claim 1, wherein said first inlet passageway is in fluid communication with said second inlet passageway.

* * * * *